United States Patent [19]
Jackson, Sr.

[11] Patent Number: 5,992,416
[45] Date of Patent: Nov. 30, 1999

[54] PORTABLE X-RAY FOUNDATION

[76] Inventor: Leon Franklin Jackson, Sr., 5808 Long Meadow Rd., Mobile, Ala. 36609

[21] Appl. No.: 09/036,654

[22] Filed: Mar. 6, 1998

[51] Int. Cl.$^6$ ..................................................... A61B 19/00
[52] U.S. Cl. .......................... 128/845; 128/846; 128/870
[58] Field of Search ..................................... 128/845, 846, 128/869, 870; 378/209; 606/238, 239, 240; 5/601

[56] References Cited

U.S. PATENT DOCUMENTS

| | | | |
|---|---|---|---|
| 4,669,106 | 5/1987 | Ammerman | 128/870 |
| 4,841,585 | 6/1989 | Masuzawa | 5/62 |
| 4,842,259 | 6/1989 | Rice | 269/323 |
| 4,912,754 | 3/1990 | Van Steenburg | 378/209 |
| 5,156,166 | 10/1992 | Sebring | 128/845 |
| 5,190,056 | 3/1993 | Hull | 128/870 |
| 5,197,975 | 3/1993 | Mombrinie | 128/845 |
| 5,385,119 | 1/1995 | Tarulli | 119/755 |
| 5,499,415 | 3/1996 | McKenna | 5/601 |
| 5,657,766 | 8/1997 | Durham | 128/870 |

Primary Examiner—Michael A. Brown
Attorney, Agent, or Firm—Joseph N. Breaux

[57] ABSTRACT

A portable X-ray foundation which is lightweight and easily placed under a patient which helps to quickly align, stabilize, and position the patient in relation to the X-ray film grid cassette. The foundation includes level indicators, alignment indicator lines for aligning the patient on the foundation in proper position with the film grid cassette thereby preventing grid-cut-off, saving considerable time, and also allowing any bed to be used for X-rays. The foundation also includes a means for securing and aligning the patient and the film grid cassette for lateral X-rays.

5 Claims, 2 Drawing Sheets

PORTABLE X-RAY FOUNDATION

TECHNICAL FIELD

The present invention relates to devices and methods for positioning patients for X-ray and more particularly to devices and methods for positioning patients for X-ray that is portable and may be utilized when the patients is lying on any type bed which when placed under a patient allows the technician to quickly align and stabilize the patient which is ultimately prevents grid-cut-off, patient sinking, and which is also ideal for decubitus and cross-table lateral views.

BACKGROUND ART

Numerous devices have been developed which assist the X-ray technician with properly positioning a patient prior to and during X-ray secessions. These prior devices recognize the need to correctly position the patient and stabilize the patient for achieving usable X-rays without the need for repetitious shots. This devices are extremely useful for situations where the patient may be mobilized and positioned on a specialized table or X-ray equipment, however a portable device, like the present invention solves many problems with positioning patients who are unable to be brought to one of these specialized imaging devices.

McKenna, U.S. Pat. No. 5,499,415 discloses a patient trauma table for use in trauma situations where the patient may be positioned for imaging and for surgical intervention. This device is extremely useful, however this device is not portable and cannot be used with existing operating beds and other hospital beds. One aspect of the present invention is that it allows the existing hospital beds to be utilized as imaging beds if necessary.

Other patient support tables are disclosed in the following Patents: Sebring, U.S. Pat. No. 5,156,166; Van Steenburg, U.S. Pat. No. 4,912,754; Rice, U.S. Pat. No. 4,842,259; and Masuzawa U.S. Pat. No. 4,841,585. Those support table recognize the problems with correctly positioning the patient for X-ray and other imaging procedures, however theses devices do not provide a simple portable device for the purpose of stabilizing a patient laying on a normal hospital bed.

Prior to the present invention, when a patient is not able to be transported the technician must attempt to properly align and stabilize the patient wherever the patient is found. The present invention solves the problem of aligning and stabilizing patients when portable X-ray equipment must be used to go to a patient, or when a patient is brought to X-ray equipment on a bed and cannot be removed from the bed.

GENERAL SUMMARY DISCUSSION OF INVENTION

It is thus an object of the invention to provide a POR-TABLE X-RAY FOUNDATION that can be used with existing hospital beds or other beds. The foundation is placed under a patient and provides a means for leveling the patient, aligning the patient, stabilizing the patient, and preventing X-ray grid-cut-off.

It is a further object of the invention to provide a POR-TABLE X-RAY FOUNDATION that is lightweight, easily stored and retrieved for usage, while also providing useful gripping handles on multiple sides of the foundation for ease of positioning the foundation under patients, while a beveled edge is also provided for easily sliding the foundation under the patient.

It is a still further object of the invention to provide a PORTABLE X-RAY FOUNDATION that includes a means for positioning X-ray grid film cassettes on edge so that X-rays may be taken from the side.

It is a still further object of the invention to provide a PORTABLE X-RAY FOUNDATION that includes visual patient and grid cassette placement indicators providing vital information to the X-ray technician concerning patient placement, alignment and stability while exposing the film.

Accordingly, a PORTABLE X-RAY FOUNDATION is provided which is constructed of light weight durable material and which is about two inches thick, thirty six inches wide and about forty inches long, includes a multiplicity of handles positioned on edges and a beveled lower edge for easily positioning the foundation under the patient, four level indicators are positioned on edges of the foundation for assuring the patients alignment with the X-ray equipment, patient placement lines in two different directions are provided for monitoring the patients position on the foundation, while lateral cassette placement grooves are provided on the foundation top surface for placing the film grid cassette on edge and taking lateral X-rays. The foundation allows for X-rays to be taken on any type bed, is particularly useful for portable X-ray procedures and in emergency situations where time is of the essence.

BRIEF DESCRIPTION OF DRAWING

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

It can be seen from the preceding description that the portable X-ray foundation can be used in a number of different imaging situations. In an emergency situation the foundation can be used to position the patient quickly saving precious time rather than transferring the patient to specialized imaging tables. The foundations beveled lower edge allows the foundation to be slid under the patient with minimal patient movement and disturbance, while the numerous handles are used to easily pull the foundation into the proper position. Levels on the foundations edges are monitored to determine when the foundation and the patient are level, while at the same time two sets of alignment indicator lines, which are perpendicular to each other, are also consulted for assuring proper alignment of the patient on the foundation and in relation to the grid cassette. The grid cassette is placed under the foundation within the alignment indicators to assure the patient and grid cassette are in proper alignment before and during exposure. When lateral views are necessary, the grid cassette is held in position on edge in slots on the foundation's top surface.

Figure 1:
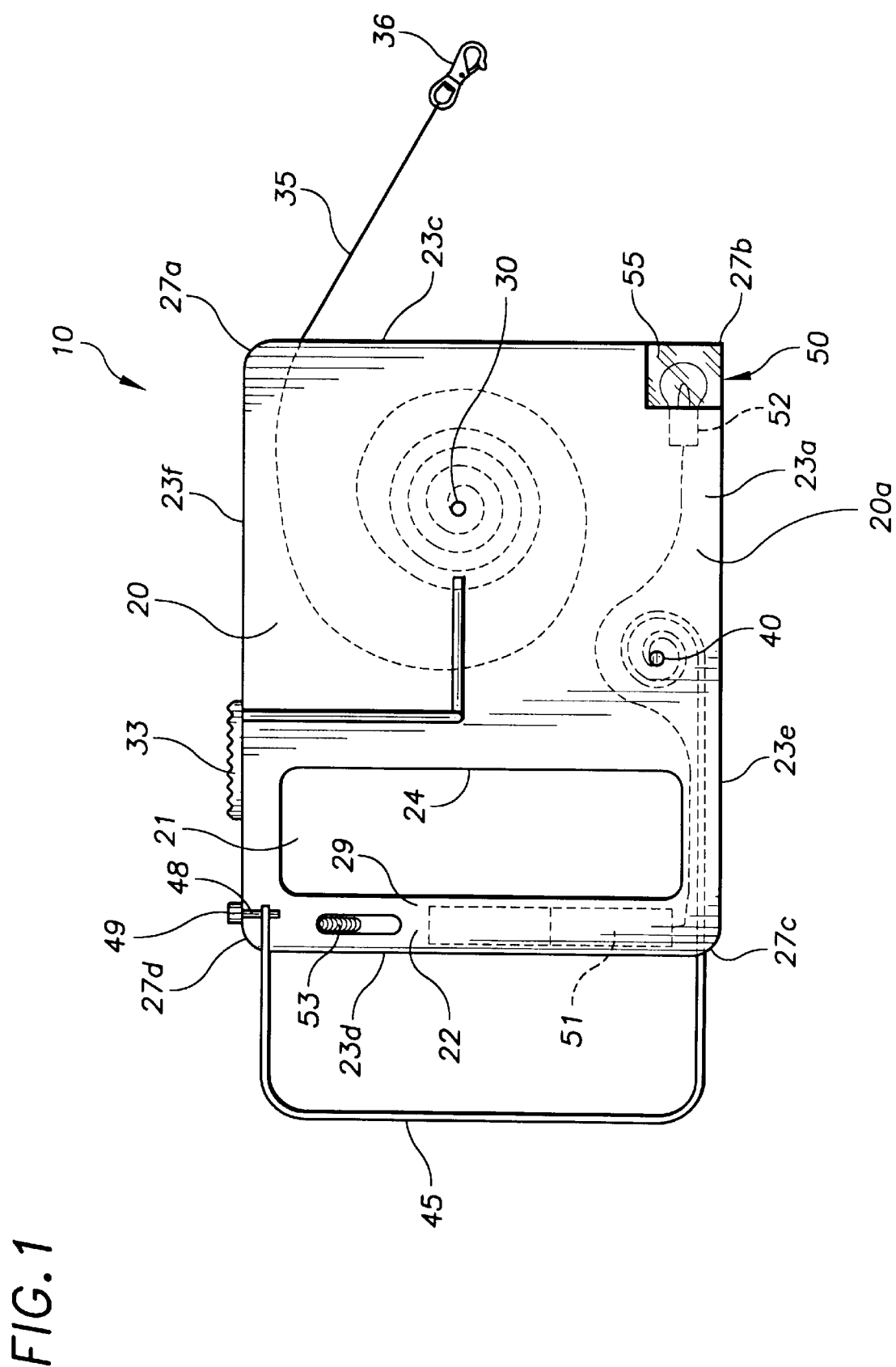
FIG. 1 illustrates the portable X-ray foundation in use on a typical hospital bed with a patient placed over it.
Figure 2:
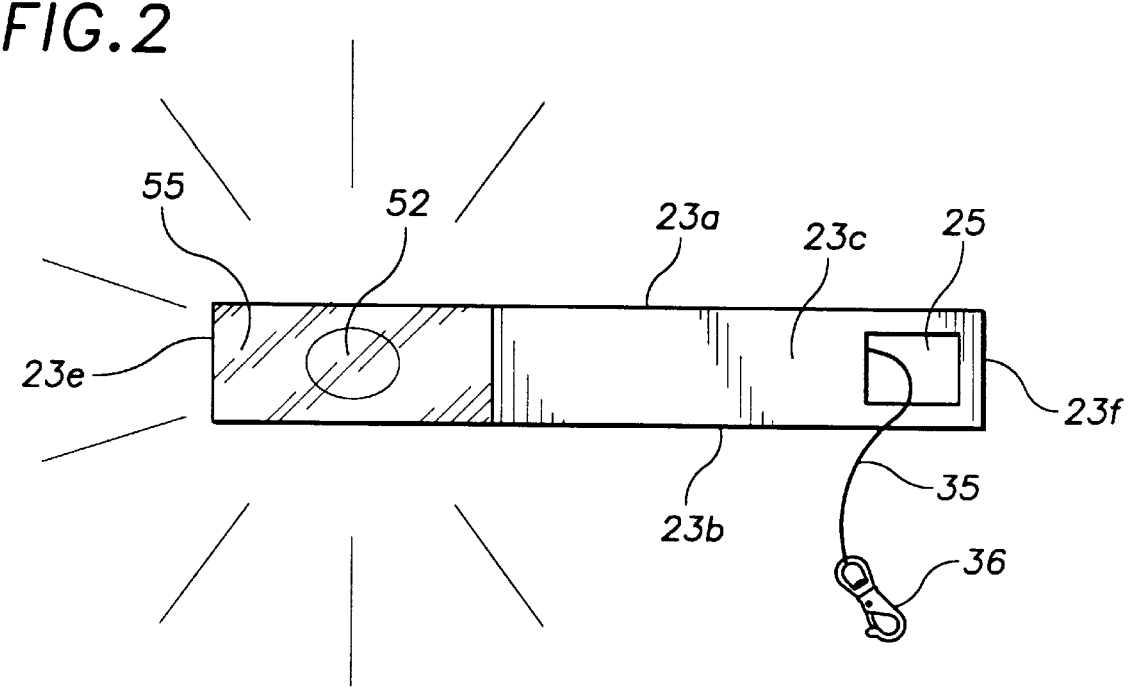
FIG. 2 is a side isometric view of the foundation.
Figure 3:
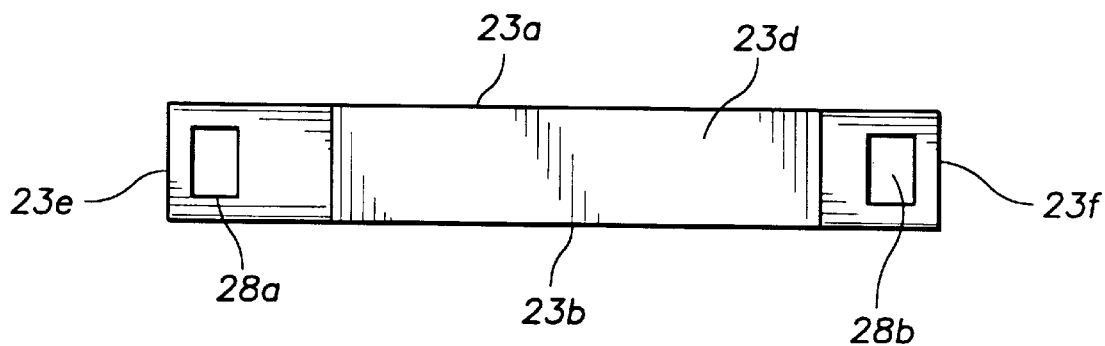
FIG. 3 is a top view of the foundation positioned on a bed.
Figure 4:
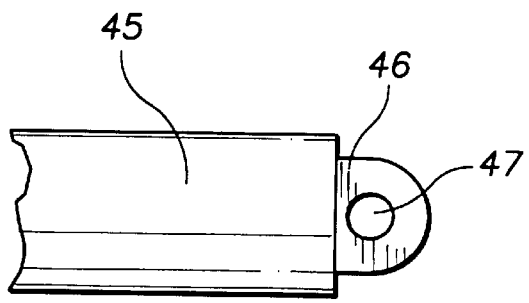
FIG. 4 is a perspective view of the foundation illustrating detailed alignment indicators, handles, lateral grid cassette slots, and the beveled lower edge.
Figure 2:
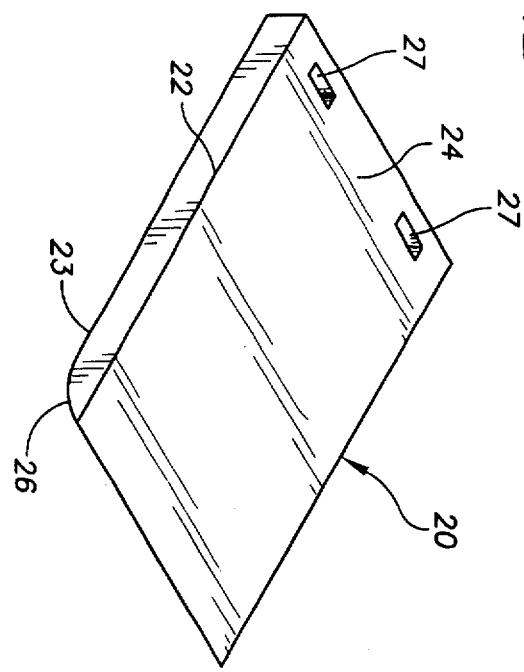
Figure 3:
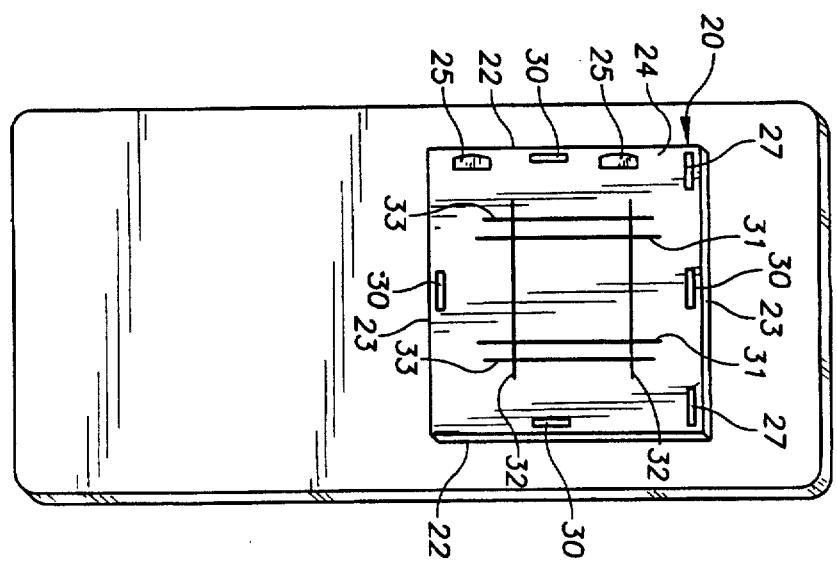
Figure 4:
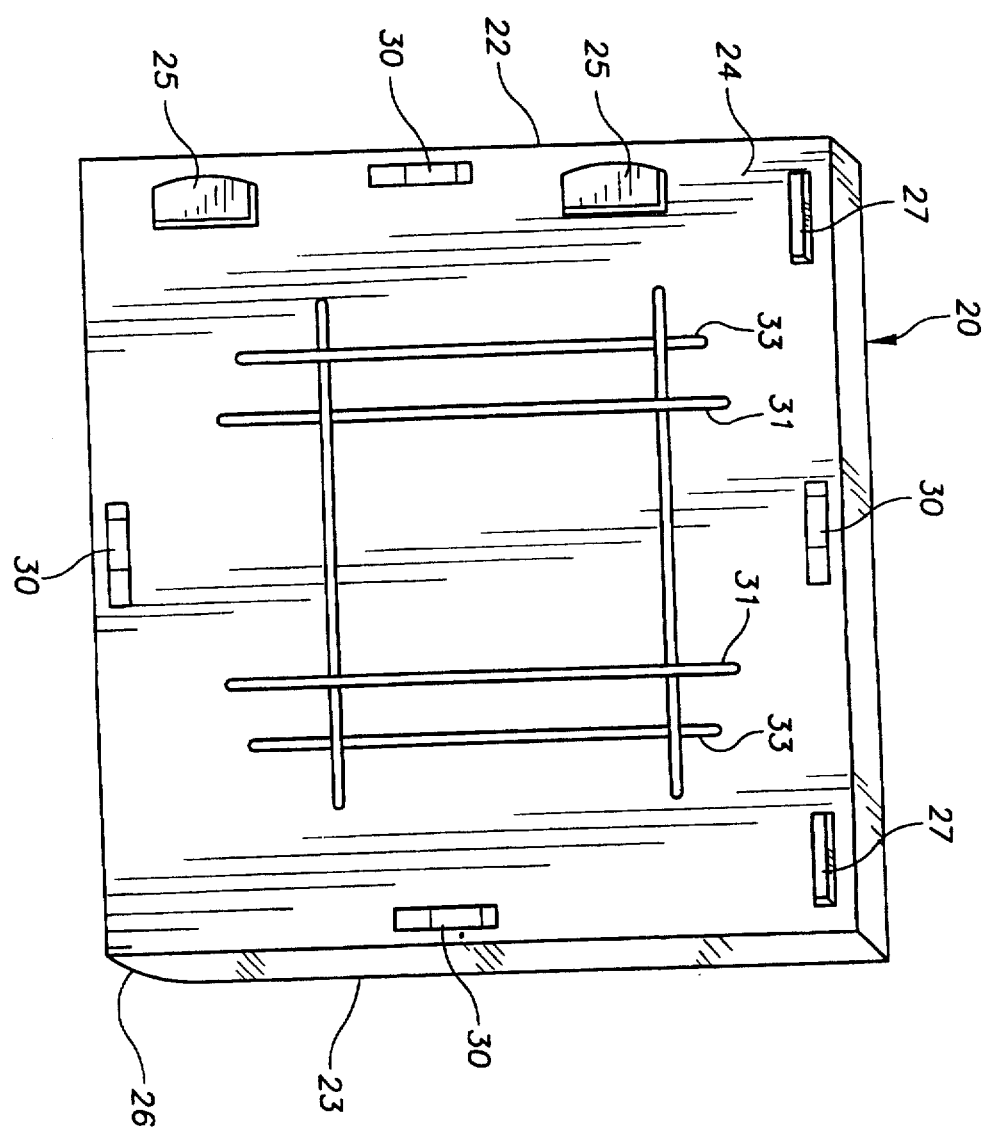

Referring to the figures in detail, the portable foundation 20 is shown generally in FIG. 1 positioned under a patient 10, on a typical hospital bed 12. The foundation 20 is rectangular in shape being about forty inches Long and about thirty six inches wide and about two inches thick.

These dimensions may vary from the disclosed preferred measurements without departing from the functionality and use of the invention. The foundation is preferably constructed of durable clear plastic using injection molding or some other suitable plastic molding technique. The material used is preferable clear acrylic plastic.

The foundation 20 includes two handles 25 positioned adjacent one of the length sides 22 which are preferably formed as part of the foundation as indentions in the top surface 24 when the foundation is molded. A beveled bottom side 26 is beveled toward the bottom surface 23 which provides a means of easily pushing the foundation under a patient who is unable to assist in the placement of the foundation. The bevel 26 is preferably about a 45° angle. The foundation also includes a means for storing the foundation by hanging from a wall which means preferably includes molded apertures 27 for hanging the foundation on hooks or the like formed adjacent to one of the two width sides 23 thereof.

Patient alignment means include four levels 30, a pair of parallel lines 31 which run the length of the foundation and another pair of parallel lines 32 which are perpendicular to lines 31 and which run parallel to the width sides 23 of the foundation. The pairs of parallel lines are preferable of different colors. For example, the pair of parallel lines which run the length of the foundation would be red while the other pair which is perpendicular to first pair would be green. The difference in color allows the technician to quickly glance at the indicators and determine which axis is in or out of alignment. Additionally, since the film grid cassette is placed under the preferably clear foundation the different color indicators allow the technician to look through the foundation while also focusing on the colored indicator lines thereby determining at a glance if the grid cassette is aligned with the alignment indicators and the patient.

The levels 30 are mounted on the top surface of the foundation and preferably flush with the top surface 24 so to prevent damage and hanging on clothing or other items which may impede sliding the foundation under the patient. The levels are also conventional bubble levels.

Lateral grid cassette slots 33 allow a grid cassette to be positioned on the foundation for lateral X-rays. The slots 33 are parallel to the alignment indicators 31 and closer to the length sides. The slots are about eighteen inches long, about one inch deep, and about one and three sixteenth inch wide. These slot dimensions allow for secure placement of the grid for the lateral shots.

It is noted that the embodiment of the PORTABLE X-RAY FOUNDATION described herein in detail for exemplary purposes is of course subject to many different variations in structure, design, application and methodology. Because many varying and different embodiments may be made with in the scope of the inventive concept(s) herein taught, and because many modifications may be made in the embodiment herein detailed in accordance with the descriptive requirements of the law, it is to be understood that the details herein are to be interpreted as illustrative and not in a limiting sense.

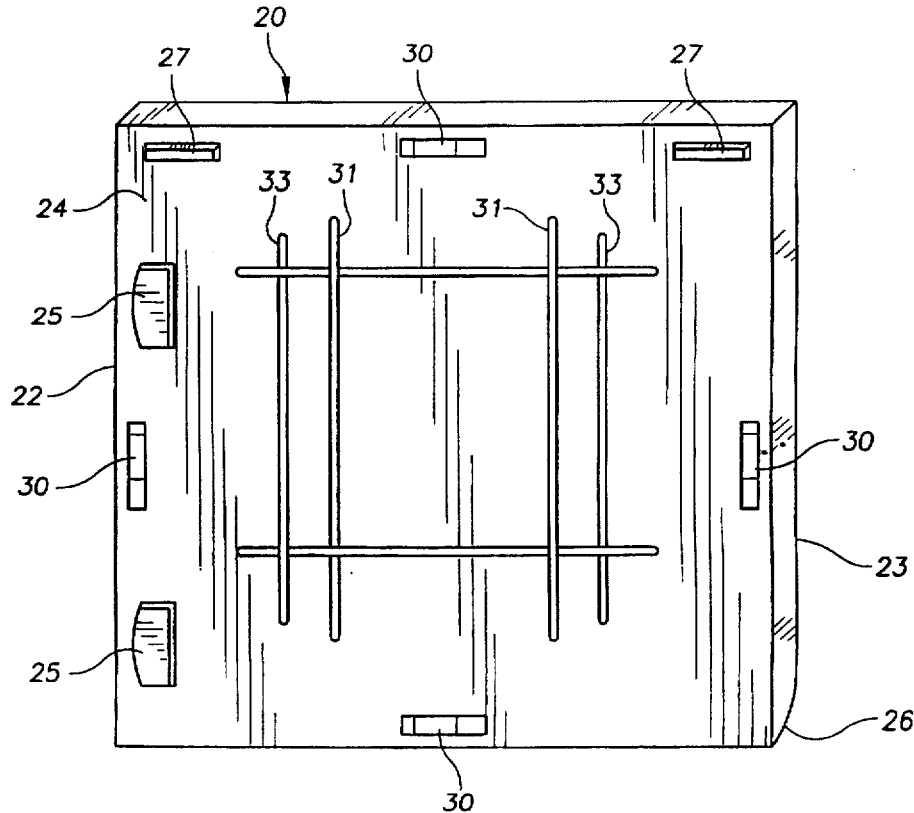

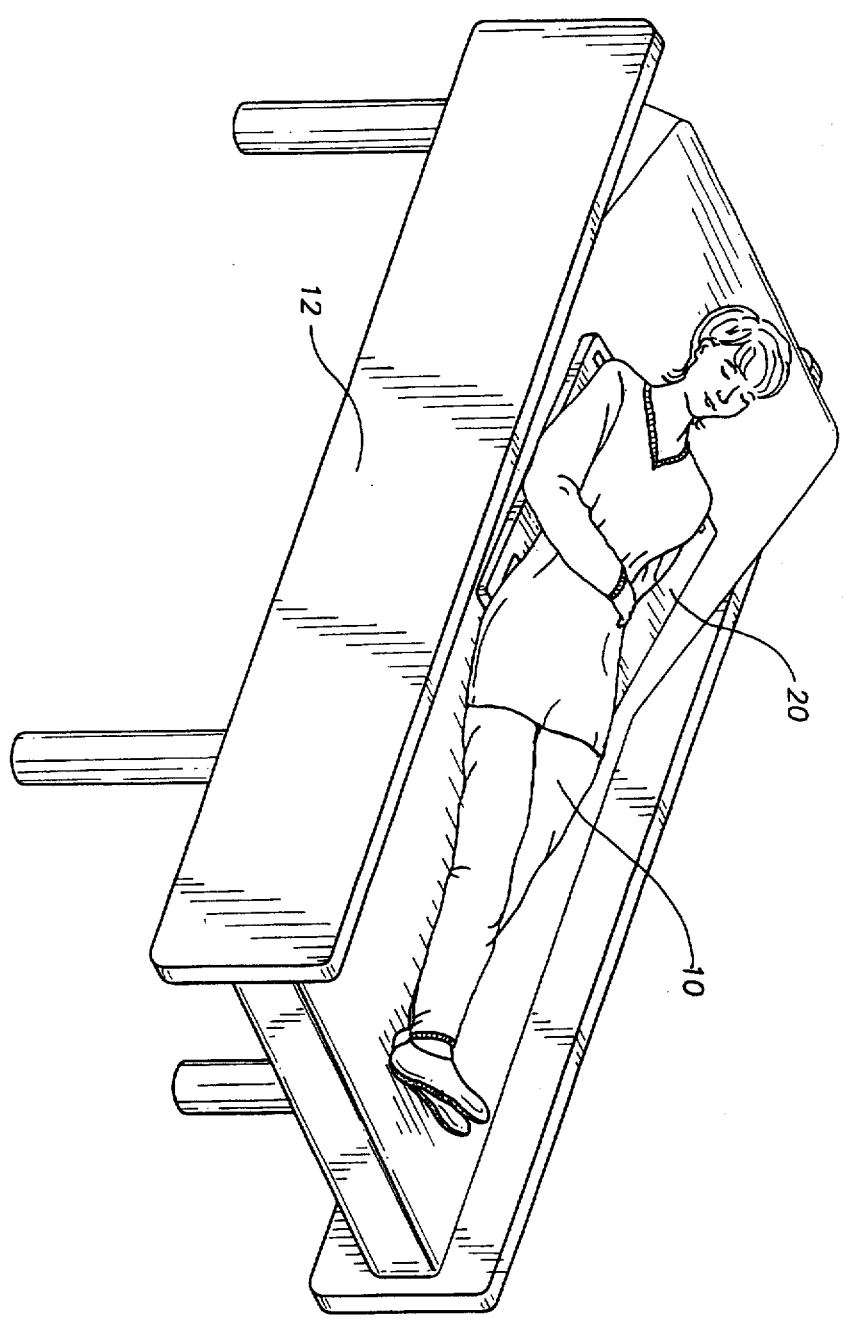

What is claimed is:

1. A portable X-ray foundation for placement under a patient on a bed which helps stabilize, level, and align the patient with the X-ray film grid cassette and the X-ray equipment, comprising:

a) a foundation member rectangular in shape and about thirty six inches wide, about forty inches long, and about two inches thick, including a foundation top surface for placing the patient, a bottom surface which sits on the bed, two length sides, two width sides, a top side and a bottom side, b) a plurality of indented handles positioned on one length side and formed as part of the foundation, c) level indicators positioned on each of the four sides of the foundation, d) a beveled bottom side beveled toward the bottom edge, e) patient alignment indicators comprising a pair of longitudinal parallel lines which run parallel to the length sides and each one about eleven inches from each of the two length sides, and another pair of alignment lines which run parallel to the width sides and perpendicular to the length lines and each one about eleven inches from each of the width sides, f) two lateral grid cassette slots positioned on the top surface and parallel to and each slot near the each length side, the slots being about eighteen inches long, about one inch deep and about one and three sixteenth inches wide, and g) foundation storing means positioned on the top side of the foundation used for hanging the foundation when not in use.

2. The portable X-ray foundation of claim 1, wherein the foundation is constructed of a durable clear plastic material so that a technician can view the grid cassette under the foundation when a patient is on the foundation top surface.

3. The portable X-ray foundation of claim 1, wherein each pair of alignment indicators is a different color from the other pair so that a technician can quickly distinguish the patient's alignment with the foundation.

4. The portable X-ray foundation of claim 1 wherein said level indicators are bubble type levels and are mounted flush with the top surface.

5. The portable X-ray foundation of claim 1 wherein there are two handles positioned on both length sides of the foundation.

* * * * *

UNITED STATES PATENT AND TRADEMARK OFFICE
CERTIFICATE OF CORRECTION

PATENT NO. : 5,992,416
DATED : November 30, 1999
INVENTOR(S) : Leon Franklin Jackson, Sr.

It is certified that error appears in the above-identified patent and that said Letters Patent is hereby corrected as shown below:

Title page,
The title page showing the illustrative figure should be deleted and replaced therefore with the attached title page.

Drawings,
Sheets 1 and 2, consisting of Figs. 1-4, should be deleted to be replaced with sheets 1-3, consisting of Figs. 1-4, as shown on the attached pages.

Signed and Sealed this

Fourteenth Day of May, 2002

*Attest:*

*Attesting Officer*

JAMES E. ROGAN
*Director of the United States Patent and Trademark Office*

United States Patent [19]
Jackson, Sr.

[11] Patent Number: 5,992,416
[45] Date of Patent: Nov. 30, 1999

[54] PORTABLE X-RAY FOUNDATION

[76] Inventor: Leon Franklin Jackson, Sr., 5808 Long Meadow Rd., Mobile, Ala. 36609

[21] Appl. No.: 09/036,654

[22] Filed: Mar. 6, 1998

[51] Int. Cl.⁶ .............................................. A61B 19/00
[52] U.S. Cl. ........................... 128/845; 128/846; 128/870
[58] Field of Search ..................................... 128/845, 846, 128/869, 870; 378/209; 606/238, 239, 240; 5/601

[56] References Cited

U.S. PATENT DOCUMENTS

| | | | |
|---|---|---|---|
| 4,669,106 | 5/1987 | Ammerman | 128/870 |
| 4,841,585 | 6/1989 | Masuzawa | 5/62 |
| 4,842,259 | 6/1989 | Rice | 269/323 |
| 4,912,754 | 3/1990 | Van Steenburg | 378/209 |
| 5,156,166 | 10/1992 | Sebring | 128/845 |
| 5,190,056 | 3/1993 | Hull | 128/870 |
| 5,197,975 | 3/1993 | Mombrinie | 128/845 |
| 5,385,119 | 1/1995 | Tarulli | 119/755 |
| 5,499,415 | 3/1996 | McKenna | 5/601 |
| 5,657,766 | 8/1997 | Durham | 128/870 |

Primary Examiner—Michael A. Brown
Attorney, Agent, or Firm—Joseph N. Breaux

[57] ABSTRACT

A portable X-ray foundation which is lightweight and easily placed under a patient which helps to quickly align, stabilize, and position the patient in relation to the X-ray film grid cassette. The foundation includes level indicators, alignment indicator lines for aligning the patient on the foundation in proper position with the film grid cassette thereby preventing grid-cut-off, saving considerable time, and also allowing any bed to be used for X-rays. The foundation also includes a means for securing and aligning the patient and the film grid cassette for lateral X-rays.

5 Claims, 2 Drawing Sheets